United States Patent [19]

Zaschke et al.

[11] 4,311,610
[45] Jan. 19, 1982

[54] LIQUID CRYSTALLINE 5-ALKYL-2 (4-ACYLOXY-PHENYL)-PYRIMIDINE

[75] Inventors: Horst Zaschke; Dietrich Demus; Adalbert Wiegeleben; Uta Böttger, all of Halle, German Democratic Rep.

[73] Assignee: VEB Werk für Fernsehelektronik im VEB Kombinat Mikroelektronik, Berlin-Oberschöneweide, German Democratic Rep.

[21] Appl. No.: 179,856

[22] Filed: Aug. 20, 1980

[30] Foreign Application Priority Data

Aug. 20, 1979 [DD] German Democratic Rep. ... 215057
Aug. 20, 1979 [DD] German Democratic Rep. ... 215058

[51] Int. Cl.$^3$ .......................... C09K 3/34; G02F 1/13; C07D 239/32
[52] U.S. Cl. .......................... 252/299.61; 252/299.5; 252/299.63; 350/350 R; 350/350 S; 544/335
[58] Field of Search .......... 252/299.5, 299.61, 299.63; 350/350 R, 350 S; 544/242, 335

[56] References Cited

U.S. PATENT DOCUMENTS

| | | | |
|---|---|---|---|
| 3,947,375 | 3/1976 | Gray et al. | 252/299.66 |
| 3,951,846 | 4/1976 | Gavrilovic | 252/299.65 |
| 3,952,046 | 4/1976 | Scherrer et al. | 252/299.66 |
| 3,997,536 | 12/1976 | Boller et al. | 252/299.61 |
| 4,062,798 | 12/1977 | Boller et al. | 252/299.61 |
| 4,112,239 | 9/1978 | Dubois et al. | 252/299.65 |
| 4,113,647 | 9/1978 | Coates et al. | 252/299.62 |
| 4,136,053 | 1/1979 | Steinstrasser | 252/299.65 |
| 4,200,580 | 4/1980 | Hsu | 252/299.61 |
| 4,229,315 | 10/1980 | Krause et al. | 252/299.63 |
| 4,256,656 | 3/1981 | Beguin et al. | 252/299.61 |

FOREIGN PATENT DOCUMENTS

| | | | |
|---|---|---|---|
| 2257588 | 6/1970 | Fed. Rep. of Germany | 252/299.61 |
| 2846409 | 6/1975 | Fed. Rep. of Germany | 252/299.61 |
| 2854310 | 6/1979 | Fed. Rep. of Germany | 252/299.63 |
| 105701 | 5/1974 | German Democratic Rep. | 252/299.63 |
| 132591 | 10/1978 | German Democratic Rep. | 252/299.61 |
| 139852 | 1/1980 | German Democratic Rep. | 252/299.61 |
| 143625 | 9/1980 | German Democratic Rep. | 252/299.61 |
| 54-6884 | 1/1979 | Japan | 252/299.63 |
| 54-11887 | 1/1979 | Japan | 252/299.61 |

OTHER PUBLICATIONS

Boller, A., et al., Mol. Cryst. Liq. Cryst., vol. 42, No. 3, pp. 215-231 (1977).
Nash, J. A., et al., Mol. Cryst. Liq. Cryst., vol. 25, pp. 299-321 (1974).
Zaschke, H., J. Prakt. Chemie, vol. 317, No. 4, pp. 617-630 (1975).
Schubert, H., et al.; J. Prakt. Chemie, vol. 312, pp. 494-506 (1970).
Bemus, D., "Nonemissive Electro-optic Displays", pp. 83-119 (1975).

Primary Examiner—Teddy S. Gron
Attorney, Agent, or Firm—Jordan and Hamburg

[57] ABSTRACT

The invention relates to the application of nematic liquid-crystalline substances in electro-optical device elements for the display of numbers, symbols and images.

Such nematic liquid crystals having low melting points and extremely high temperatures of transparency.

The nematic liquid-crystalline substances are 5-alkyl-2-[4-acyloxyphenyl]-pyrimidines having the general formula

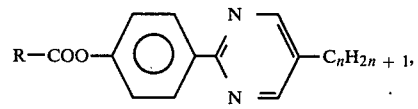

wherein

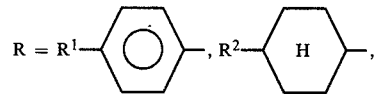

$R^1 = C_nH_{2n+1}$, $C_nH_{2n+1}O$, $C_nH_{2n+1}OCOO$, $C_nH_{2n+1}COO$, $C_nH_{2n+1}S$, F, Cl, Br, NO$_2$, CN CF$_3$
$R^2 = C_nH_{2n+1}$ n denotes any of the numbers between 1 and 10.

These substituted pyrimidines are used in electro-optical device elements singly or as mixtures of each other, as well as mixtures with other liquid-crystalline or non liquid-crystalline components.

22 Claims, No Drawings

LIQUID CRYSTALLINE 5-ALKYL-2 (4-ACYLOXY-PHENYL)-PYRIMIDINE

The invention relates to the application of nematic liquid crystalline substances in electro-optical arrangements for the modulation of incident or transmitted light and for the display of numbers, symbols and images.

BACKGROUND OF THE INVENTION

It is known that nematic liquid crystals show various electro-optical effects due to their dielectrical anisotropy in electrical fields (G. Meier, J. G. Grabmaier, Application of Liquid Crystals, Berlin-Heidelberg-New York, Springer Verlag 1975). Modulation of light may be obtained in appropriate cells by aid of these effects as well as a display of numbers, symbols and images.

Nematic liquid crystals with negative dielectrical anisotropy show the dynamic dispersive effect which allows the construction of electro-optical elements without the use of polarizers. In nematic liquid crystals with positive dielectrical anisotropy, the Schadt-Helfrich effect occurs, which is based upon the deformation of artifically distorted nematic layers in electrical fields. This arrangement needs two polarizing filters.

Presently, no pure compound nor a mixture of a plurality of substances is known which could fulfill all demands which are required from a substance for electro-optical elements, particularly low melting temperatures and high temperatures of transparency. The properties of mixtures may be improved because the melting point of eutectic mixtures diminish with the number of components. The temperatures of transparency of mixtures may be raised considerably by the addition of substances with high temperatures of transparency.

OBJECT OF THE INVENTION

The object of the invention is to provide new nematic liquid crystals, having low melting points and extremely high points of transparency, for use in electro-optical devices, as well as methods for their production.

It was found that liquid-crystalline 5-alkyl-2-[4-acyloxy-phenyl]-pyrimidines of the general formula

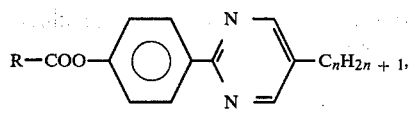

where

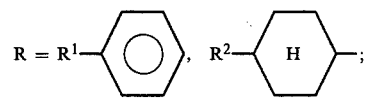

$R^1 = C_nH_{2n+1}$, $C_nH_{2n+1}O$, $C_nH_{2n+1}OCOO$, $C_nH_{2n+1}COO$, $C_nH_{2n+1}S$, F, Cl, Br, $NO_2$, CN, $CF_3$ $R^2 = C_nH_{2n+1}$ and n denotes the numbers from 1 to 10 are provided according to the invention.

The 5-alkyl-2-[4-acyloxy-phenyl]-pyrimidines are used in electro-optical elements as mixtures of themselves as well as, preferably, mixtures with other liquid-crystalline components or mixtures with non-liquid-crystalline components.

The advantage of the substances used according to the invention is that they possess high temperatures of transparency as well as sufficiently low melting points. They are stable against the influence of air, water, elevated temperatures and light, which is very advantageous for their use in LCD components.

The invention will be explained by six examples:

EXAMPLE 1

Examples of the substances, substituted according to the invention, are tabulated herebelow:

TABLE 1

$R^1$—⟨phenyl⟩—COO—⟨phenyl⟩—pyrimidine—$C_nH_{2n+1}$

| N | $R^1$ | n | K | S | N | $I_S$ |
|---|---|---|---|---|---|---|
| 1 | $C_6H_{13}$— | 5 | . 57 | — | . 157 | . |
| 2 | $C_6H_{13}$— | 6 | . 43 | — | . 147 | . |
| 3 | $C_6H_{13}$— | 7 | . 64 | — | . 150 | . |
| 4 | $C_6H_{13}$— | 8 | . 75.5 | — | . 142.5 | . |
| 5 | $CH_3$—O— | 6 | . 116 | — | . 196.5 | . |
| 6 | $C_3H_7O$— | 6 | . 103 | — | . 187 | . |
| 7 | $C_7H_{15}O$— | 6 | . 72.5 | — | . 166 | . |
| 8 | $CH_3$— | 6 | . 99 | — | . 116.5 | . |
| 9 | Br— | 6 | . 120 | — | . 181 | . |
| 10 | Cl— | 6 | . 118 | — | . 182 | . |
| 11 | F— | 6 | . 116.5 | — | . 149 | . |
| 12 | $CH_3S$— | 6 | . 110 | — | . 141 | . |
| 13 | $CH_3COO$— | 6 | . 83 | — | . 195 | . |
| 14 | $CH_3OCOO$— | 6 | . 88 | — | . 200 | . |
| 15 | $CF_3$ | 6 | . 102 | . 151 | . 160.5 | . |
| 16 | $NO_2$ | 7 | . 147 | . 223 | . 229 | . |
| 17 | CN | 8 | . 144 | . 159.5 | . 240 | . |

K = crystalline-solid;
N = nematic
S = smectic;
$I_S$ = isotropic-liquid

TABLE 2

$R^1$—⟨H⟩—COO—⟨phenyl⟩—pyrimidine—$R^2$

| $R^1$ | $R^2$ | K | N | $I_S$ |
|---|---|---|---|---|
| $CH_3$— | $C_6H_{13}$ | . 98 | . 141 | . |
| $C_5H_{11}$ | $C_5H_{11}$ | . 97 | . 185 | . |

EXAMPLE 2

A mixture of three components, n-propylcyclohexanecarboxylic acid-4-cyano-phenyl ester 34.5 mol%, n-butylcyclohexanecarboxylic acid-4-cyano-phenyl ester 31.0 mol%, and n-pentylcyclohexanecarboxylic acid-4-cyano-phenyl ester 34.5 mol%, designated as Mi 14, possesses the following properties:

Melting point +12.5° to 16° C., Point of transparency: 72° C., and Threshold Voltage 1.3 V (f=500 Hz at 25° C.).

A mixture of the following composition, Mi 14 80 mol%, 5-n-hexyl-2-[4-n-hexylbenzoyloxy-phenyl]-pyrimidine (#2 in table 1) 20 mol%, has the following properties:

Melting point +13.5° to 25° C., highly supercoolable, at −18° C., crystallization begins only after 6 to 7 hours, Point of transparency: +94° C., Threshold Voltage: 1.69 V (f=500 Hz at 24° C.).

EXAMPLE 3

A mixture of Mi 14 90 mol%, and 5-n-hexyl-2-[4-n-hexylbenzoyloxyphenyl]-pyrimidine (#2 in table 1) 10 mol%, possesses positive dielectric anisotropy and shows the Schadt-Helfrich effect in transposed layers has a Melting point +3.5° to 9° C., Point of Transparency: 80° to 81° C., and Threshold voltage: 1.78 V (500 Hz at 24° C.).

The mixture is highly supercoolable and crystallizes at −18° C. after only several hours.

EXAMPLE 4

Preparation of 5-n-alkyl-2-[4-hydroxyphenyl]-pyrimidines.

17.4 g (0.1 mol) 4-hydroxybenzamidine hydrochloride and 0.1 mol of the respective α-alkyl-β-dimeethylaminoacrolein are added under stirring to a sodium methylate solution, consisting of 9.2 g (0.4 g-atoms) sodium in 80 ml absolute methanol. The solution is boiled for six hours under reflux. The reaction mixture is then concentrated in a rotary evaporator, mixed with 100 ml dilute acetic acid and then repeatedly extracted with ether. The etheric extract is washed with water, dried over $Na_2SO_4$ and evaporated until dry. The dry residue is crystallized from n-hexane.

TABLE 3

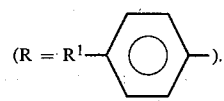

| n | Yield % | F °C. |
|---|---|---|
| 5 | 89 | 131 |
| 6 | 95 | 95 |
| 7 | 93 | 88 |
| 8 | 96 | 79 |

EXAMPLE 5

Preparation of 5-n-alkyl-2-[4-(4-subst.-benzoyloxy)-phenyl)pyrimidines $(R = R^1 - \bigcirc -)$.

0.01 mol compound No. 3 and 0.02 mol substituted benzoylchloride are added to a sodium methylate solution of 0.23 g (0.01 g-atoms) sodium in 30 ml absolute methanol. The reaction mixture is stirred for ten hours at room temperature and left standing overnight. After addition of water, the mixture is extracted with ether. The ether extract is washed, treated with $Na_2SO_4$ and activated carbon and concentrated until dry. The residue is recrystallized several times from n-hexane or chromatographed in an $Al_2O_3$-column (activity degree 1) with ether or methylenechloride and crystallized from an n-hexane solution after removal of the other solvents.

TABLE 4

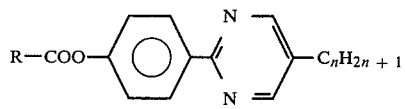

| $R^1$ | n | Yield % | K | S | N | I |
|---|---|---|---|---|---|---|
| $C_6H_{13}-$ | 5 | 73 | . 57 | | . 157 | . |
| $C_6H_{13}-$ | 6 | 70 | . 43 | | . 147 | . |
| $C_6H_{13}-$ | 7 | 95 | . 64 | | . 150 | . |
| $C_6H_{13}-$ | 8 | 78 | . 75.5 | | . 142.5 | . |
| $CH_3O-$ | 6 | 90 | . 116 | | . 196.5 | . |
| $C_3H_7O-$ | 6 | 81 | . 103 | | . 187 | . |
| $C_7H_{15}O-$ | 6 | 86 | . 72.5 | | . 166 | . |
| $CH_3-$ | 6 | 81 | . 99 | | . 165 | . |
| Br— | 6 | 90 | . 120 | | . 181 | . |
| Cl— | 6 | 88 | . 118 | | . 182 | . |
| F— | 6 | 75 | . 116.5 | | . 149 | . |
| $CH_3S-$ | 6 | 68 | . 110 | | . 141 | . |
| $CH_3COO-$ | 6 | 65 | . 83 | | . 195 | . |
| $CH_3OCOO-$ | 6 | 55 | . 88 | | . 200 | . |
| $CF_3$ | 6 | 68 | . 102 | . 151 | . 160.5 | . |
| $NO_2$ | 7 | 78 | . 147 | . 223 | . 229 | . |
| CN | 8 | 70 | .144 | . 159.5 | . 240 | . |

K = crystalline-solid
N = nematic
I = isotropic-liquid
Transition temperatures in °C.

EXAMPLE 6

Preparation of 5-alkyl-2-[4-(4-subst.-cyclohexylcarbonyloxy)-phenyl) pyrimidines.

Synthesis and purification are handled analogously to Example 2 but using 4-subst.-cyclohexanecarboxylic acyl chlorides.

TABLE 5

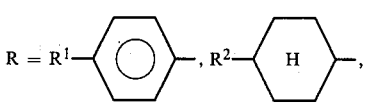

| $R^1$ | $R^2$ | Yield % | K | N | I |
|---|---|---|---|---|---|
| $CH_3-$ | $C_6H_{13}$ | 72 | . 98 | . 141 | . |
| $C_5H_{11}-$ | $C_5H_{11}-$ | 80 | . 97 | . 185 | . |

We claim:

1. 5-alkyl-2-(4-acyloxyphenyl)-pyrimidines of the general formula

R—COO—⟨○⟩—pyrimidine—$C_nH_{2n+1}$ wherein $R = R^1-\bigcirc-, R^2-\langle H \rangle-,$ $R^1 = C_nH_{2n+1}, C_nH_{2n+1}O, C_nH_{2n+1}OCOO, C_nH_{2n+1}COO, C_nH_{2n+1}S, F, Cl, Br, NO_2, CN, CF_3,$ $R^2 = C_nH_{2n+1}$ n=1 to 10.

2. A 5-alkyl-2-(4-acyloxyphenyl)-pyrimidine according to claim 1, substituted as follows:

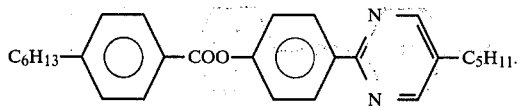

3. A 5-alkyl-2-(4-acyloxyphenyl)-pyrimidine according to claim 1, substituted as follows:

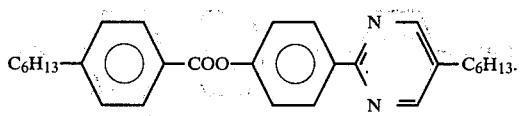

4. A 5-alkyl-2-(4-acyloxyphenyl)-pyrimidine according to claim 1, substituted as follows:

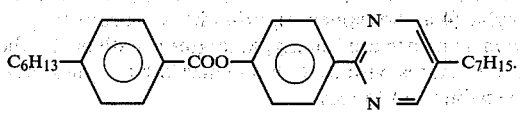

5. A 5-alkyl-2-(4-acyloxyphenyl)-pyrimidine according to claim 1, substituted as follows:

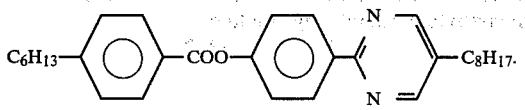

6. A 5-alkyl-2-(4-acyloxyphenyl)-pyrimidine according to claim 1, substituted as follows:

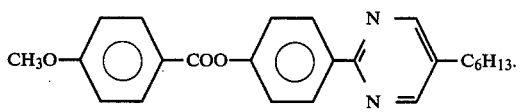

7. A 5-alkyl-2-(4-acyloxyphenyl)-pyrimidine according to claim 1, substituted as follows:

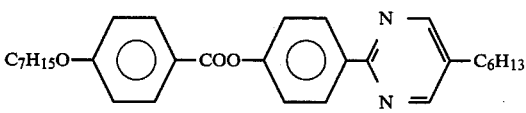

8. A 5-alkyl-2-(4-acyloxyphenyl)-pyrimidine according to claim 1, substituted as follows:

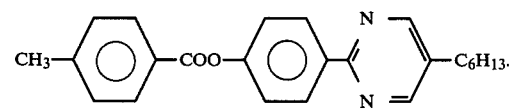

9. A 5-alkyl-2-(4-acyloxyphenyl)-pyrimidine according to claim 1, substituted as follows:

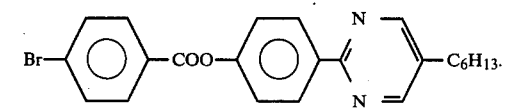

10. A 5-alkyl-2-(4-acyloxyphenyl)-pyrimidine according to claim 1, substituted as follows:

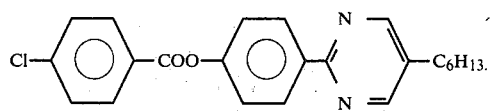

11. A 5-alkyl-2-(4-acyloxyphenyl)-pyrimidine according to claim 1, substituted as follows:

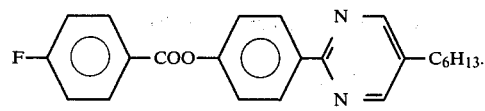

12. A 5-alkyl-2-(4-acyloxyphenyl)-pyrimidine according to claim 1, substituted as follows:

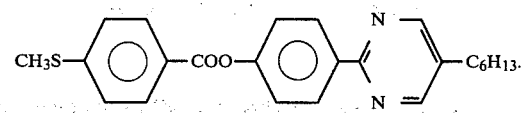

13. A 5-alkyl-2-(4-acyloxyphenyl)-pyrimidine according to claim 1, substituted as follows:

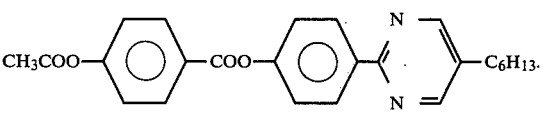

14. A 5-alkyl-2-(4-acyloxyphenyl)-pyrimidine according to claim 1, substituted as follows:

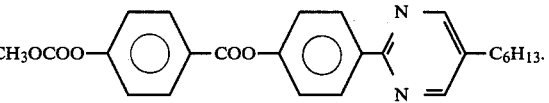

15. A 5-alkyl-2-(4-acyloxyphenyl)-pyrimidine according to claim 1, substituted as follows:

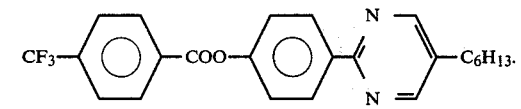

16. A 5-alkyl-2-(4-acyloxyphenyl)-pyrimidine according to claim 1, substituted as follows:

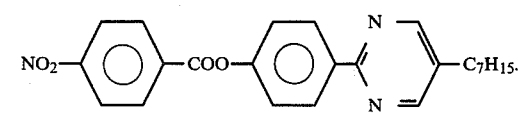

17. A 5-alkyl-2-(4-acyloxyphenyl)-pyrimidine according to claim 1, substituted as follows:

18. A 5-alkyl-2-(4-acyloxyphenyl)-pyrimidine according to claim 1, substituted as follows:

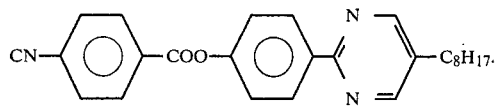

19. A 5-alkyl-2-(4-acyloxyphenyl)-pyrimidine according to claim 1, substituted as follows:

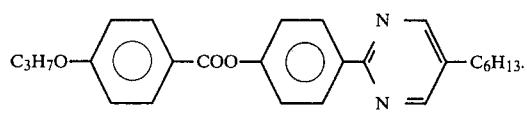

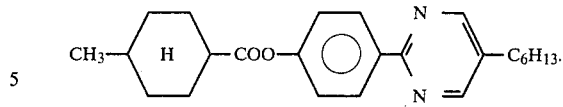

20. A 5-alkyl-2-(4-acyloxyphenyl)-pyrimidine according to claim 1, substituted as follows:

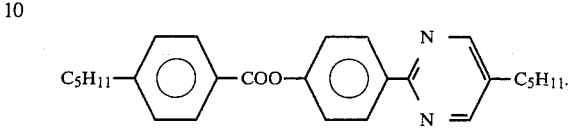

21. An electro-optical device containing nematic liquid crystalline substances for the modulation of incident or transmitted light and for the display of numbers, symbols and images, wherein said substances are 5-alkyl-2-(4-acyloxyphenyl)pyrimidines according to claim 1 and are used singly, in mixtures with each other, or in mixtures with other liquid crystalline or non-liquid crystalline substances.

22. An electro-optical device of claim 21, wherein a mixture is used of n-propylcyclohexanecarboxylic acid-4-cyanophenylester, n-butylcyclohexanecarboxylic acid-4-cyanophenylester, n-pentylcyclohexanecarboxylic acid-4-cyano-phenylester and 5-n-hexyl-2-(4-n-hexylbenzoyloxyphenyl)-pyrimidine.

* * * * *